(12) United States Patent
Borovinskih et al.

(10) Patent No.: US 10,893,918 B2
(45) Date of Patent: Jan. 19, 2021

(54) DETERMINING A DENTAL TREATMENT DIFFICULTY

(71) Applicant: Align Technology, Inc., San Jose, CA (US)

(72) Inventors: Artem Borovinskih, San Jose, CA (US); Roman A. Roschin, Moscow (RU); Rene M. Sterental, Palo Alto, CA (US); Dmitriy Ten, Novosibirsk (RU)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 14/982,413

(22) Filed: Dec. 29, 2015

(65) Prior Publication Data

US 2016/0106520 A1    Apr. 21, 2016

Related U.S. Application Data

(63) Continuation of application No. 13/410,182, filed on Mar. 1, 2012, now Pat. No. 9,220,580.

(51) Int. Cl.
*A61C 7/00* (2006.01)
*G16H 15/00* (2018.01)
*G16H 50/50* (2018.01)

(52) U.S. Cl.
CPC ............ *A61C 7/002* (2013.01); *G16H 15/00* (2018.01); *G16H 50/50* (2018.01)

(58) Field of Classification Search
CPC combination set(s) only.
See application file for complete search history.

(56) References Cited

U.S. PATENT DOCUMENTS

| 2,171,695 A | 9/1939 | Harper |
| 2,194,790 A | 3/1940 | Gluck |
| 2,467,432 A | 4/1949 | Kesling |

(Continued)

FOREIGN PATENT DOCUMENTS

| AU | 517102 B | 11/1977 |
| AU | 3031677 A | 11/1977 |

(Continued)

OTHER PUBLICATIONS

Collins English Dictionary, Definition of teeth, 2017, Collins English Dictionary, pp. 1-3.*

(Continued)

*Primary Examiner* — Omar F Fernandez Rivas
*Assistant Examiner* — Bernard E Cothran
(74) *Attorney, Agent, or Firm* — Shay Glenn LLP

(57) ABSTRACT

Embodiments for determining a dental treatment difficulty are described herein. One method embodiment includes receiving an initial and subsequent position of each of a first tooth and a second tooth and calculating a change in position of each of the first tooth and the second tooth. The method embodiment can also include projecting the changes in position of each of the first tooth and the second tooth onto a reference line and calculating a change in position on the reference line for the first tooth and the second tooth. The method embodiment can further include determining the dental treatment difficulty based on the changes in position on the reference line.

18 Claims, 4 Drawing Sheets

(56) References Cited

U.S. PATENT DOCUMENTS

| | | |
|---|---|---|
| 2,531,222 A | 11/1950 | Kesling |
| 3,089,487 A | 5/1963 | Enicks et al. |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,055,895 A | 11/1977 | Huge |
| 4,117,596 A | 10/1978 | Wallshein |
| 4,134,208 A | 1/1979 | Pearlman |
| 4,139,944 A | 2/1979 | Bergersen |
| 4,179,811 A | 12/1979 | Hinz |
| 4,183,141 A | 1/1980 | Dellinger |
| 4,195,046 A | 3/1980 | Kesling |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |

(56) References Cited

U.S. PATENT DOCUMENTS

| | | |
|---|---|---|
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Stayer et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,212,435 B1 | 4/2001 | Lattner et al. |
| 6,217,334 B1 | 4/2001 | Hultgren |
| 6,227,850 B1 | 5/2001 | Chishti et al. |
| 6,230,142 B1 | 5/2001 | Benigno et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |

(56) References Cited

U.S. PATENT DOCUMENTS

| | | |
|---|---|---|
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinhold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,984,128 B2 | 1/2006 | Breining et al. |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,217,131 B2 | 5/2007 | Vuillemot |
| 7,220,122 B2 | 5/2007 | Chishti |
| 7,220,124 B2 | 5/2007 | Taub et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |

(56) References Cited

U.S. PATENT DOCUMENTS

| | | |
|---|---|---|
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,108,189 B2 | 1/2012 | Chelnokov et al. |
| 8,118,592 B2 | 2/2012 | Tortorici |
| 8,126,025 B2 | 2/2012 | Takeda |
| 8,144,954 B2 | 3/2012 | Quadling et al. |
| 8,152,518 B2 | 4/2012 | Kuo |
| 8,160,334 B2 | 4/2012 | Thiel et al. |
| 8,172,569 B2 | 5/2012 | Matty et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,277,972 B2 | 3/2016 | Brandt et al. |
| 9,336,336 B2 | 5/2016 | Deichmann et al. |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,506,808 B2 | 11/2016 | Jeon et al. |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 10,123,706 B2 | 11/2018 | Elbaz et al. |
| 10,123,853 B2 | 11/2018 | Moss et al. |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,248,883 B2 | 4/2019 | Borovinskih et al. |
| 10,258,432 B2 | 4/2019 | Webber |
| 10,275,862 B2 | 4/2019 | Levin |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0042038 A1 | 4/2002 | Miller et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0068598 A1 | 4/2003 | Vallittu et al. |
| 2003/0095697 A1 | 5/2003 | Wood et al. |
| 2003/0101079 A1* | 5/2003 | McLaughlin ............ A61C 7/00 705/3 |
| 2003/0103060 A1 | 6/2003 | Anderson et al. |
| 2003/0120517 A1 | 6/2003 | Eida et al. |

(56) References Cited

U.S. PATENT DOCUMENTS

| | | |
|---|---|---|
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0042569 A1 | 2/2005 | Plan et al. |
| 2005/0048432 A1* | 3/2005 | Choi .................. A61C 7/002 433/24 |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0003907 A1 | 1/2007 | Chishti et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0072144 A1* | 3/2007 | Imgrund .................. A61C 7/00 433/24 |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0215582 A1 | 9/2007 | Roeper et al. |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057462 A1* | 3/2008 | Kitching .................. A61C 7/00 433/24 |
| 2008/0057467 A1 | 3/2008 | Gittelson |
| 2008/0057479 A1 | 3/2008 | Grenness |
| 2008/0059238 A1 | 3/2008 | Park et al. |
| 2008/0062429 A1 | 3/2008 | Liang et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1* | 12/2008 | Kitching .................. A61C 7/00 704/2 |
| 2009/0029310 A1 | 1/2009 | Pumphrey et al. |
| 2009/0030290 A1 | 1/2009 | Kozuch et al. |
| 2009/0030347 A1 | 1/2009 | Cao |

(56) References Cited

U.S. PATENT DOCUMENTS

| | | |
|---|---|---|
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0210032 A1 | 8/2009 | Beiski et al. |
| 2009/0218514 A1 | 9/2009 | Klunder et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0045902 A1 | 2/2010 | Ikeda et al. |
| 2010/0068676 A1* | 3/2010 | Mason .................. A61C 19/04 433/215 |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0065060 A1 | 3/2011 | Teixeira et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0266326 A1 | 10/2013 | Joseph et al. |
| 2013/0286174 A1 | 10/2013 | Urakabe |
| 2013/0293824 A1 | 11/2013 | Yoneyama et al. |
| 2013/0325431 A1 | 12/2013 | See et al. |
| 2013/0337412 A1 | 12/2013 | Kwon |
| 2014/0081091 A1 | 3/2014 | Abolfathi et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0186794 A1 | 7/2014 | Deichmann et al. |
| 2014/0280376 A1 | 9/2014 | Kuo |
| 2014/0294273 A1 | 10/2014 | Jaisson |
| 2015/0002649 A1 | 1/2015 | Nowak et al. |
| 2015/0004553 A1 | 1/2015 | Li et al. |
| 2015/0132708 A1 | 5/2015 | Kuo |
| 2015/0173856 A1 | 6/2015 | Iowe et al. |
| 2015/0182303 A1 | 7/2015 | Abraham et al. |
| 2015/0230885 A1 | 8/2015 | Wucher |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2016/0003610 A1 | 1/2016 | Lampert et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0246936 A1 | 8/2016 | Kahn |
| 2016/0287358 A1 | 10/2016 | Nowak et al. |
| 2016/0302885 A1 | 10/2016 | Matov et al. |
| 2016/0338799 A1 | 11/2016 | Wu et al. |
| 2016/0367339 A1 | 12/2016 | Khardekar et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0071705 A1 | 3/2017 | Kuo |
| 2017/0100212 A1 | 4/2017 | Sherwood et al. |
| 2017/0100213 A1 | 4/2017 | Kuo |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0319296 A1 | 11/2017 | Webber et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071055 A1 | 3/2018 | Kuo |
| 2018/0125610 A1 | 5/2018 | Carrier et al. |
| 2018/0153648 A1 | 6/2018 | Shanjani et al. |
| 2018/0153649 A1 | 6/2018 | Wu et al. |

(56) References Cited

U.S. PATENT DOCUMENTS

| | | |
|---|---|---|
| 2018/0153733 A1 | 6/2018 | Kuo |
| 2018/0168788 A1 | 6/2018 | Fernie |
| 2018/0192877 A1 | 7/2018 | Atiya et al. |
| 2018/0280118 A1 | 10/2018 | Cramer |
| 2018/0284727 A1 | 10/2018 | Cramer et al. |
| 2018/0318043 A1 | 11/2018 | Li et al. |
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0029522 A1 | 1/2019 | Sato et al. |
| 2019/0029784 A1 | 1/2019 | Moalem et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076026 A1 | 3/2019 | Elbaz et al. |
| 2019/0076214 A1 | 3/2019 | Nyukhtikov et al. |
| 2019/0076216 A1 | 3/2019 | Moss et al. |
| 2019/0090983 A1 | 3/2019 | Webber et al. |
| 2019/0095539 A1 | 3/2019 | Elbaz et al. |
| 2019/0099129 A1 | 4/2019 | Kopelman et al. |
| 2019/0105130 A1 | 4/2019 | Grove et al. |
| 2019/0125494 A1 | 5/2019 | Li et al. |

FOREIGN PATENT DOCUMENTS

| | | |
|---|---|---|
| CA | 1121955 A1 | 4/1982 |
| CN | 1655732 A | 8/2005 |
| CN | 1655733 A | 8/2005 |
| CN | 102017658 A | 4/2011 |
| CN | 103889364 A | 6/2014 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| ES | 463897 A1 | 1/1980 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 04-028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| KR | 10-20020062793 A | 7/2002 |
| KR | 10-20090065778 A | 6/2009 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |

OTHER PUBLICATIONS

Dictionary.com, Definition of Plural, 2017, Dictionary.com, pp. 1-4.*
Dictionary.com, Define Quadrant, 2017, Dictionary.com, pp. 1-5.*
Turnquist et al., Dental Arch, 2019, ScienceDirect, pp. 1-18 (Year: 2019).*
AADR. American Association for Dental Research; Summary of Activities; Los Angeles, CA; p. 195; Mar. 20-23,(year of pub. sufficiently earlier than effective US filing date and any foreign priority date) 1980.
Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.
Alexander et al.; The DigiGraph Work Station Part 2 Clinical Management; J. Clin. Orthod.; pp. 402-407; (Author Manuscript); Jul. 1990.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.
Allesee Orthodontic Appliances: DuraClearTM; Product information; 1 page; (year of pub. sufficiently earlier than effective US filing date and any foreign priority date) 1997.
Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

(56) References Cited

OTHER PUBLICATIONS

Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm) Mar. 2004.
Begole et al.; A Computer System for the Analysis of Dental Casts; The Angle Orthodontist; 51(3); pp. 252-258; Jul. 1981.
Berland; The use of smile libraries for cosmetic dentistry; Dental Tribune: Asia Pacific Edition; pp. 16-18; Mar. 29, 2006.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(1); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bookstein; Principal warps: Thin-plate splines and decomposition of deformations; IEEE Transactions on pattern analysis and machine intelligence; 11(6); pp. 567-585; Jun. 1989.
Bourke, Coordinate System Transformation; 1 page; retrived from the internet (http://astronomy.swin.edu.au/' pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on The Uses of the Computer in Orthodontic Practice (Part 2); journal of Clinical Orthodontics; 13(8); pp. 539-551 (interview); Aug. 1979.
Cadent Inc.; OrthoCAD ABO user guide; 38 pages; Dec. 21, 2005.
Cadent Inc.; Reviewing and modifying an orthoCAD case; 4 pages; Feb. 14, 2005.
Cardinal Industrial Finishes; Powder Coatings; 6 pages; retrieved from the Internet (http://www.cardinalpaint.com) on Aug. 25, 2000.
Carnaghan, An Alternative to Holograms for the Portrayal of Human Teeth; 4th Int'l Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret A Man With a Vision, Part 3: The Computer Gives New Vision—Literally, Part 4: Bytes 'N Bites The Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.

(56) References Cited

OTHER PUBLICATIONS

CSI Computerized Scanning and Imaging Facility; What is a maximum/minimum intensity projection (MIP/MinIP); 1 page; retrieved from the internet (http://csi.whoi.edu/content/what-maximumminimum-intensity-projection-mipminip); Jan. 4, 2010.

Cureton; Correcting Malaligned Mandibular Incisors with Removable Retainers; Journal of Clinical Orthodontics; 30(7); pp. 390-395; Jul. 1996.

Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.

Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.

Daniels et al.; The development of the index of complexity outcome and need (ICON); British Journal of Orthodontics; 27(2); pp. 149-162; Jun. 2000.

DCS Dental AG; The CAD/CAM 'DCS Titan System' for Production of Crowns/Bridges; DSC Production; pp. 1-7; Jan. 1992.

Defranco et al.; Three-Dimensional Large Displacement Analysis of Orthodontic Appliances; Journal of Biomechanics; 9(12); pp. 793-801; Jan. 1976.

Dental Institute University of Zurich Switzerland; Program for International Symposium on Computer Restorations: State of the Art of the CEREC-Method; 2 pages; May 1991.

Dentrac Corporation; Dentrac document; pp. 4-13; (year of pub. sufficiently earlier than effective US filing date and any foreign priority date) 1992.

Dentrix; Dentrix G3, new features; 2 pages; retrieved from the Internet (http://www.dentrix.com/g3/new_features/index.asp); on Jun. 6, 2008.

Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.

Dicom to surgical guides; (Screenshot)1 page; retrieved from the internet at YouTube (https://youtu.be/47KtOmCEFQk); Published Apr. 4, 2016.

Di Giacomo et al.; Clinical application of sterolithographic surgical guides for implant placement: Preliminary results; Journal Periodontolgy; 76(4); pp. 503-507; Apr. 2005.

Di Muzio et al.; Minimum intensity projection (MinIP); 6 pages; retrieved from the internet (https://radiopaedia.org/articles/minimum-intensity-projection-minip) on Sep. 6, 2018.

Doruk et al.; The role of the headgear timer in extraoral co-operation; European Journal of Orthodontics; 26; pp. 289-291; Jun. 1, 2004.

Doyle; Digital Dentistry; Computer Graphics World; pp. 50-52 and p. 54; Oct. 2000.

Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.

Duret et al.; CAD/CAM Imaging in Dentistry; Current Opinion in Dentistry; 1 (2); pp. 150-154; Apr. 1991.

Duret et al; CAD-CAM in Dentistry; Journal of the American Dental Association; 117(6); pp. 715-720; Nov. 1988.

Duret; The Dental CAD/CAM, General Description of the Project; Hennson International Product Brochure, 18 pages; Jan. 1986.

Duret; Vers Une Prosthese Informatisee; Tonus; 75(15); pp. 55-57; (English translation attached); 23 pages; Nov. 15, 1985.

Economides; The Microcomputer in the Orthodontic Office; Journal of Clinical Orthodontics; 13(11); pp. 767-772; Nov. 1979.

Elsasser; Some Observations on the History and Uses of the Kesling Positioner; American Journal of Orthodontics; 36(5); pp. 368-374; May 1, 1950.

English translation of Japanese Laid-Open Publication No. 63-11148 to inventor T. Ozukuri (Laid-Open on Jan. 18, 1998) pp. 1-7.

Faber et al.; Computerized Interactive Orthodontic Treatment Planning; American Journal of Orthodontics; 73(1); pp. 36-46; Jan. 1978.

Felton et al.; A Computerized Analysis of the Shape and Stability of Mandibular Arch Form; American Journal of Orthodontics and Dentofacial Orthopedics; 92(6); pp. 478-483; Dec. 1987.

Friede et al.; Accuracy of Cephalometric Prediction in Orthognathic Surgery; Journal of Oral and Maxillofacial Surgery; 45(9); pp. 754-760; Sep. 1987.

Friedrich et al; Measuring system for in vivo recording of force systems in orthodontic treatment-concept and analysis of accuracy; J. Biomech.; 32(1); pp. 81-85; (Abstract Only) Jan. 1999.

Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.

Gansky; Dental data mining: potential pitfalls and practical issues; Advances in Dental Research; 17(1); pp. 109-114; Dec. 2003.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

Geomagic; Dental reconstruction; 1 page; retrieved from the internet (http://geomagic.com/en/solutions/industry/detal_desc.php) on Jun. 6, 2008.

Gim-Alldent Deutschland, "Das DUX System: Die Technik," 3 pages; (English Translation Included); (year of pub. sufficiently earlier than effective US filing date and any foreign priority date); 2002.

Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Gottschalk et al.; OBBTree: A hierarchical structure for rapid interference detection; 12 pages; (http://www.cs.unc.edu/?geom/OBB/OBBT.html); retrieved from te internet (https://www.cse.iitk.ac.in/users/amit/courses/RMP/presentations/dslamba/presentation/sig96.pdf) on Apr. 25, 2019.

gpsdentaire.com; Get a realistic smile simulation in 4 steps with GPS; a smile management software; 10 pages; retrieved from the internet (http://www.gpsdentaire.com/en/preview/) on Jun. 6, 2008.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Grest, Daniel; Marker-Free Human Motion Capture in Dynamic Cluttered Environments from a Single View-Point, PhD Thesis; 171 pages; Dec. 2007.

Guess et al.; Computer Treatment Estimates in Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa..); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

(56) References Cited

OTHER PUBLICATIONS

Huckins; CAD-CAM Generated Mandibular Model Prototype from MRI Data; AAOMS, p. 96; (Abstract Only); (year of pub. sufficiently earlier than effective US filing date and any foreign priority date) 1999.

Invisalign; You were made to move. There's never been a better time to straighten your teeth with the most advanced clear aligner in the world; Product webpage; 2 pages; retrieved from the internet (www.invisalign.com/) on Dec. 28, 2017.

JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Karaman et al.; A practical method of fabricating a lingual retainer; Am. Journal of Orthodontic and Dentofacial Orthopedics; 124(3); pp. 327-330; Sep. 2003.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kumar et al.; Rapid maxillary expansion: A unique treatment modality in dentistry; J. Clin. Diagn. Res.; 5(4); pp. 906-911; Aug. 2011.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

Mantzikos et al.; Case report: Forced eruption and implant site development; The Angle Orthodontist; 68(2); pp. 179-186; Apr. 1998.

McCann; Inside the ADA; J. Amer. Dent. Assoc, 118:286-294; Mar. 1989.

McNamara et al.; Invisible Retainers; J. Clin Orthod.; pp. 570-578; 11 pages; (Author Manuscript); Aug. 1985.

Mcnamara et al.; Orthodontic and Orthopedic Treatment in the Mixed Dentition; Needham Press; pp. 347-353; Jan. 1993.

Methot; Get the picture with a gps for smile design in 3 steps; Spectrum; 5(4); pp. 100-105; (year of pub. sufficiently earlier than effective US filng date and any foreign priority date) 2006.

Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.

Moles; Correcting Mild Malalignments—As Easy As One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; CEREC CAD/CAM Inlays: Aesthetics and Durability in a Single Appointment; Dentistry Today; 9(8); pp. 20, 22-23 and 54; Oct. 1990.

Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Ogawa et al.; Mapping, profiling and clustering of pressure pain threshold (PPT) in edentulous oral muscosa; Journal of Dentistry; 32(3); pp. 219-228; Mar. 2004.

Ogimoto et al.; Pressure-pain threshold determination in the oral mucosa; Journal of Oral Rehabilitation; 29(7); pp. 620-626; Jul. 2002.

ormco.com; Increasing clinical performance with 3D interactive treatment planning and patient-specific appliances; 8 pages; retrieved from the internet (http://www.konsident.com/wp-content/files_mf/1295385693http_ormco.com_index_cmsfilesystemaction_fileOrmcoPDF_whitepapers.pdf) on Feb. 27, 2019.

OrthoCAD downloads; retrieved Jun. 27, 2012 from the Internet (www.orthocad.com/download/downloads.asp); 2 pages; Feb. 14, 2005.

Page et al.; Validity and accuracy of a risk calculator in predicting periodontal disease; Journal of the American Dental Association; 133(5); pp. 569-576; May 2002.

Patterson Dental; Cosmetic imaging; 2 pages retrieved from the Internet (http://patterson.eaglesoft.net/cnt_di_cosimg.html) on Jun. 6, 2008.

Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.

Pinkham; Foolish Concept Propels Technology; Dentist, 3 pages , Jan./Feb. 1989.

Pinkham; Inventor's CAD/CAM May Transform Dentistry; Dentist; pp. 1 and 35, Sep. 1990.

Ponitz; Invisible retainers; Am. J. Orthod.; 59(3); pp. 266-272; Mar. 1971.

Procera Research Projects; Procera Research Projects 1993 ' Abstract Collection; 23 pages; (year of pub. sufficiently earlier than effective US filing date and any foreign priority date) 1993.

Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.

(56) References Cited

OTHER PUBLICATIONS

Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Rudge; Dental Arch Analysis: Arch Form, A Review of the Literature; The European Journal of Orthodontics; 3(4); pp. 279-284; Jan. 1981.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Sarment et al.; Accuracy of implant placement with a sterolithographic surgical guide; journal of Oral and Maxillofacial Implants; 118(4); pp. 571-577; Jul. 2003.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_ The smile-vision cosmetic imaging system; 2 pages; retrieved from the internet (http://www.smile-vision.net/cos_imaging.php) on Jun. 6, 2008.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
The American Heritage, Stedman's Medical Dictionary; Gingiva; 3 pages; retrieved from the interent (http://reference.com/search/search?q=gingiva) on Nov. 5, 2004.
Thera Mon; "Microsensor"; 2 pages; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(Tm) Appliance System; The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(a); pp. 769-778; (year of pub. sufficiently earlier than effective US filing date and any foreign priority date); 1993.
Varady et al.; Reverse Engineering of Geometric Models' An Introduction; Computer-Aided Design; 29(4); pp. 255-268; 20 pages; (Author Manuscript); Apr. 1997.

(56) References Cited

OTHER PUBLICATIONS

Verstreken et al.; An Image-Guided Planning System for Endosseous Oral Implants; IEEE Transactions on Medical Imaging; 17(5); pp. 842-852; Oct. 1998.

Vevin et al.; Pose estimation of teeth through crown-shape matching; In Medical Imaging: Image Processing of International Society of Optics and Photonics; vol. 4684; pp. 955-965; May 9, 2002.

Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.

Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.

Warunek et.al.; Clinical Use of Silicone Elastomer Applicances; JCO; 23(10); pp. 694-700; Oct. 1989.

Watson et al.; Pressures recorded at to denture base-mucosal surface interface in complete denture wearers; Journal of Oral Rehabilitation 14(6); pp. 575-589; Nov. 1987.

Wells; Application of the Positioner Appliance in Orthodontic Treatment; American Journal of Orthodontics; 58(4); pp. 351-366; Oct. 1970.

Wiedmann; According to the laws of harmony to find the right tooth shape with assistance of the computer; Digital Dental News; 2nd Vol.; pp. 0005-0008; (English Version Included); Apr. 2008.

Wikipedia; Palatal expansion; 3 pages; retrieved from the internet (https://en.wikipedia.org/wiki/Palatal_expansion) on Mar. 5, 2018.

Williams; Dentistry and CAD/CAM: Another French Revolution; J. Dent. Practice Admin.; 4(1); pp. 2-5 Jan./Mar. 1987.

Williams; The Switzerland and Minnesota Developments in CAD/CAM; Journal of Dental Practice Administration; 4(2); pp. 50-55; Apr./Jun. 1987.

Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.

Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.

Wolf; Three-dimensional structure determination of semitransparent objects from holographic data; Optics Communications; 1(4); pp. 153-156; Sep. 1969.

Wong et al.; Computer-aided design/computer-aided manufacturing surgical guidance for placement of dental implants: Case report; Implant Dentistry; 16(2); pp. 123-130; Sep. 2007.

Wong et al.; The uses of orthodontic study models in diagnosis and treatment planning; Hong Kong Dental Journal; 3(2); pp. 107-115; Dec. 2006.

WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.

Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.

Yaltara Software; Visual planner; 1 page; retrieved from the internet (http://yaltara.com/vp/) on Jun. 6, 2008.

Yamada et al.; Simulation of fan-beam type optical computed-tomography imaging of strongly scattering and weakly absorbing media; Applied Optics; 32(25); pp. 4808-4814; Sep. 1, 1993.

Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.

Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.

Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.

Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.

Yoshii; Research on a New Orthodontic Appliance: the Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.

Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.

Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.

Zhang et al.; Visual speech features extraction for improved speech recognition; 2002 IEEE International conference on Acoustics, Speech and Signal Processing; vol. 2; 4 pp.; May 13-17, 2002.

Zhou et al.; Biofuel cells for self-powered electrochemical biosensing and logic biosensing: A review; Electroanalysis; 24(2); pp. 197-209; Feb. 2012.

Zhou et al.; Bio-logic analysis of injury biomarker patterns in human serum samples; Talanta; 83(3); pp. 955-959; Jan. 15, 2011.

Morton et al.; U.S. Appl. No. 16/177,067 entitled "Dental appliance having selective occlusal loading and controlled intercuspation," filed Oct. 31, 2018.

Akopov et al.; U.S. Appl. No. 16/178,491 entitled "Automatic treatment planning," filed Nov. 1, 2018.

O'Leary et al.; U.S. Appl. No. 16/195,701 entitled "Orthodontic retainers," filed Nov. 19, 2018.

Shanjani et al., U.S. Appl. No. 16/206,894 entitled "Sensors for monitoring oral appliances," filed Nov. 28, 2019.

Shanjani et al., U.S. Appl. No. 16/231,906 entitled "Augmented reality enhancements for dental practitioners." Dec. 24, 2018.

Kopleman et at., U.S. Appl. No. 16/220,381 entitled "Closed loop adaptive orthodontic treatment methods and apparatuses," Dec. 14, 2018.

Sabina et al., U.S. Appl. No. 16/258,516 entitled "Diagnostic intraoral scanning" filed Jan. 25, 2019.

Sabina et al., U.S. Appl. No. 16/258,523 entitled "Diagnostic intraoral tracking" filed Jan. 25, 2019.

Sabina et al., U.S. Appl. No. 16/258,527 entitled "Diagnostic intraoral methods and apparatuses" filed Jan. 25, 2019.

Culp; U.S. Appl. No. 16/236,220 entitled "Laser cutting," filed Dec. 28, 2018.

Culp; U.S. Appl. No. 16/265,287 entitled "Laser cutting," filed Feb. 1, 2019.

Arnone et al.; U.S. Appl. No. 16/235,449 entitled "Method and system for providing indexing and cataloguing of orthodontic related treatment profiles and options," filed Dec. 28, 2018.

Mason et al.; U.S. Appl. No. 16/374,648 entitled "Dental condition evaluation and treatment," filed Apr. 3, 2019.

Brandt et al.; U.S. Appl. No. 16/235,490 entitled "Dental wire attachment," filed Dec. 28, 2018.

Kuo; U.S. Appl. No. 16/270,891 entitled "Personal data file," filed Feb. 8, 2019.

Dentalwings; Intraoral scanner; 7 pages; retrieved from the internet (https://web.archive.org/web/20160422114335/http://www.dentalwings.com/products/intraoral-scanner/); available as of Apr. 4, 2016.

Dentalwings; I series dental impression scanner; 8 pages; retrieved from the internet (https://web.archive.org/web/20160502145908/

(56) References Cited

OTHER PUBLICATIONS http://www.dentalwings.com/products/scan-and-design-systems/iseries/); available as of May 2, 2016.
3 Shape Trios 3; Insane speed-scanning with 3shape trios 3 intracral canner; (Screenshot); 2 pages; retrieved from the internet at You Tube (https//www.youtube.com/watch?v=X5CviUZ5DPQ&feature=youtu.be; available as of Sep. 18, 2015.

* cited by examiner

DETERMINING A DENTAL TREATMENT DIFFICULTY

PRIORITY INFORMATION

This application is a Continuation of U.S. application Ser. No. 13/410,182, filed Mar. 1, 2012, the entire contents of which are hereby incorporated by reference.

TECHNICAL FIELD

The present disclosure relates to systems and methods for determining a dental treatment difficulty.

BACKGROUND

The present disclosure relates generally to the field of dental treatment. More specifically, the present disclosure relates to determining a treatment difficulty.

Some objectives in the field of dental treatment are to realign a patient's teeth to positions where the teeth function well and/or align the teeth to provide a pleasing aesthetic appearance. One goal of a treatment provider can be to take the patient's dentition from a starting arrangement to a final arrangement. In such processes, treatment providers may need to correct a patient's anterior-posterior movement within a quadrant of teeth.

For many treatment providers, knowing how difficult a treatment will be can be useful in dental treatment planning. For example, it can indicate to a treatment provider the length of treatment, what dental appliances may be needed, and/or whether the treatment professional has the proper training and/or is capable of treating the patient.

DETAILED DESCRIPTION

Figure 1A:
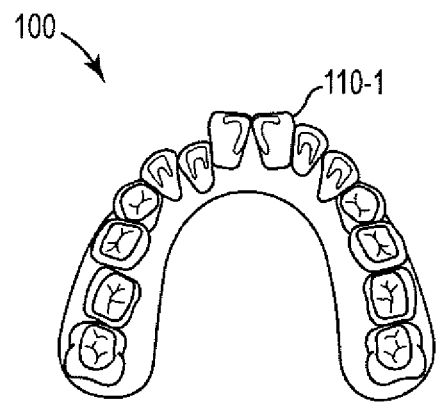
FIG. 1A illustrates an initial virtual dental model according to one or more embodiments of the present disclosure.

Embodiments of the present disclosure include computing device related, system, and method embodiments for determining dental treatment difficulty. For example, one or more method embodiments include, receiving an initial and subsequent position of each of a first tooth and a second tooth and calculating a change in position of each of the first tooth and the second tooth. One or more method embodiments can also include projecting the changes in position of each of the first tooth and the second tooth onto a reference line and calculating a change in position on the reference line for the first tooth and the second tooth. One or more method embodiments can further include determining the dental treatment difficulty based on the changes in position on the reference line.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that changes may be made without departing from the scope of the present disclosure.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense. As used herein, "a", "at least one", "a number of" something can refer to one or more such things.

Anterior-posterior (A-P) correction is a movement of teeth in a quadrant (e.g., upper left, upper right, lower left, lower right) when movements of teeth in a segment of the quadrant between a first molar and a canine, along an arch are all in a distal direction (e.g., toward the last tooth in a quadrant of a dental arch) or all in a mesial direction (e.g., direction toward an anterior midline in a dental arch). Estimating a treatment difficulty of A-P correction can, as discussed above, aid in predicting and/or adjusting a treatment plan of a patient.

Based on root movement measurements, an amount of mesial and/or distal movement of canine and posterior teeth for a quadrant can be calculated for a patient. Having average mesial and/or distal movement of a posterior tooth and a canine, based on prior completed dental treatments on other patients, as well as a table of treatment difficulty ranges can allow for estimating a level of treatment difficulty for a quadrant of teeth. This level and the calculated value of A-P correct can be presented to a treatment provider for use in treatments and treatment planning.

In various embodiments, with the use of computer graphic software, a treatment professional can establish a custom treatment target specific to a particular tooth of a particular patient. With this treatment target in mind, a dental treatment difficulty can be determined.

Virtual dental models from a scan of a patient's dentition can be provided with computer-aided tooth-treatment systems. An initial digital data set (IDDS) representing an initial tooth arrangement may be obtained in a variety of ways.

For example, the patient's teeth may be imaged to obtain digital data using direct and/or indirect structured light, X-rays, three-dimensional X-rays, lasers, destructive scanning, computer-aided tomographic images or data sets, magnetic resonance images, intra-oral scanning technology, photographic reconstruction, and/or other imaging techniques. The IDDS can include an entire mouth tooth arrangement, some, but not all teeth in the mouth, and/or it can include a single tooth.

A positive model and/or negative impression of the patient's teeth or a tooth may be scanned using an X-ray, laser scanner, destructive scanner, structured light, and/or other range acquisition system to produce the IDDS. The data set produced by the range acquisition system may be converted to other formats to be compatible with the software which is used for manipulating images within the data set, as described herein.

Referring now to FIG. 1A, there is illustrated an initial dental model 100 (e.g., an initial virtual dental model)

according to one or more embodiments of the present disclosure. As described herein, the initial dental model 100 can be obtained prior to treatment or at an intermediate state of treatment (e.g., before treatment has been completed).

One or more embodiments of the present disclosure include receiving a virtual IDDS and a desired position of a tooth contained in the virtual IDDS. The initial dental model 100 (e.g., virtual IDDS) can also include a model of an individual tooth (e.g., tooth 110-1) that is part of a full dental model, such as full dental model 100.

Figure 1B:
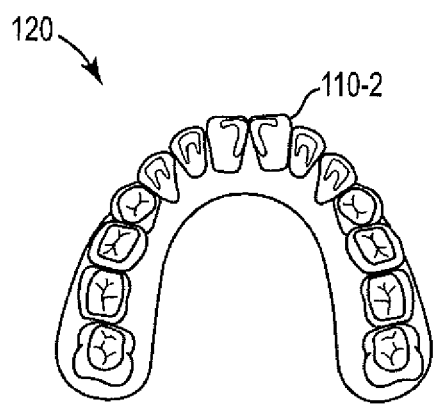
FIG. 1B illustrates a target virtual dental model corresponding to the initial virtual dental model illustrated in FIG. 1A according to the present disclosure.

FIG. 1B illustrates a target dental model 120 (e.g., a target virtual dental model) corresponding to the initial dental model illustrated in FIG. 1A according to the present disclosure. The target dental model 120 can be created by modifying the initial dental model 100 according to one or more treatment goals.

The one or more treatment goals can be case-specific (e.g., specific to the particular patient on which the initial dental model 100 was based). A target dental model can also include a target model of an individual tooth (e.g., tooth 110-2) that is part of a full dental model similar to full target dental model 120. In some embodiments, a virtual IDDS and a target virtual dental model can be displayed via a user interface in three dimensions.

Manual visual estimation of a patient's teeth can also be used in collecting information regarding an initial dental model and target dental model. For example, a treatment provider may take manual measurements of the patient's dentition or one or more particular teeth when determining a difficulty of a particular dental treatment.

Figure 2:
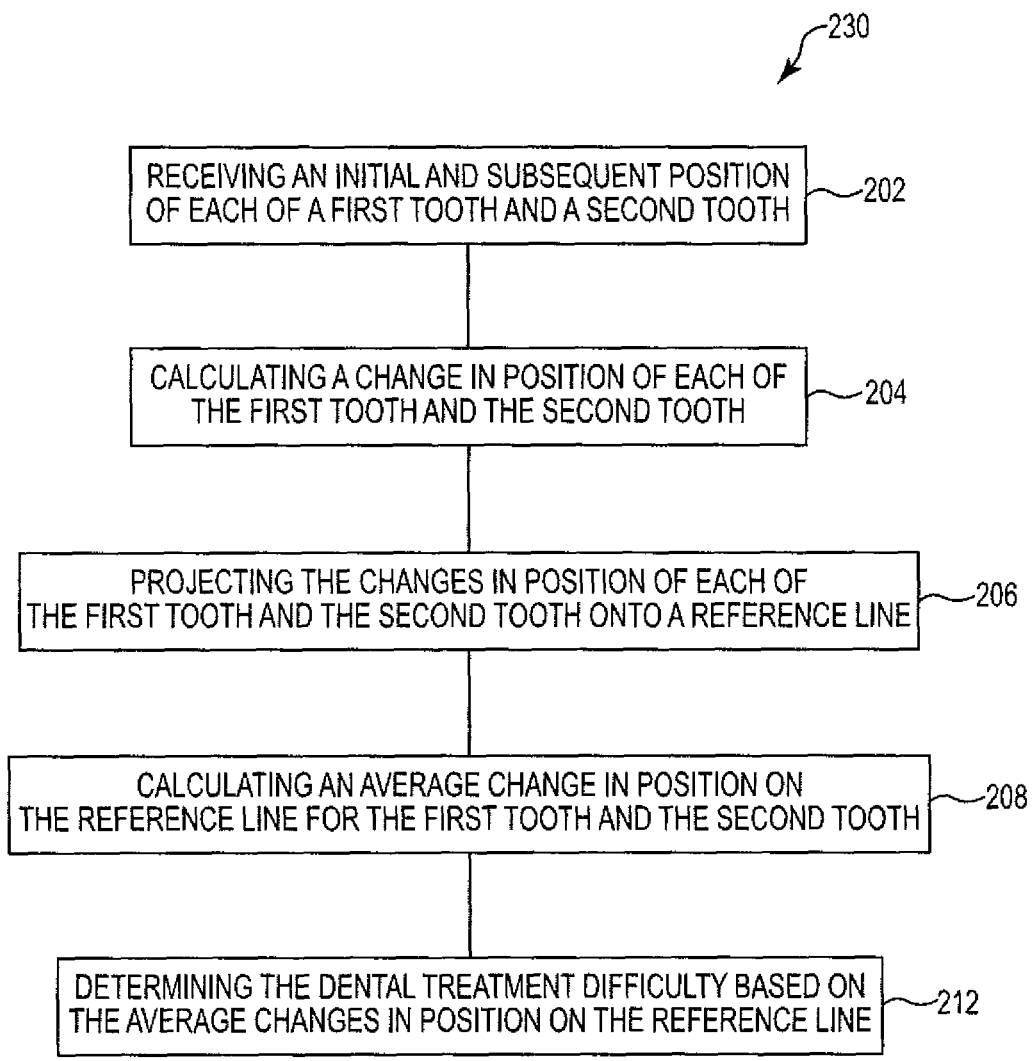
FIG. 2 illustrates an example method for determining a dental treatment difficulty according to one or more embodiments of the present disclosure.

FIG. 2 illustrates an example method 230 for determining a dental treatment difficulty according to one or more embodiments of the present disclosure. At 202, an initial and subsequent position of each of a first tooth and a second tooth is received.

In various embodiments, the first tooth may be a canine tooth, and the second tooth may be a posterior tooth (e.g., a molar). The initial tooth position can be a current tooth position of a patient, and the subsequent position can be a desired tooth position. For example, a patient and his or her treatment provider may plan to have the patient's teeth aligned to a particular desired position.

At 204, a change in position of each of the first tooth and the second tooth is calculated. The changes in position can include mesial and/or distal position changes. For example, calculating the changes in position can include changes along an x and/or y axis, but not a z axis.

The distance between a center point of a tooth (e.g., the first and/or second tooth) in an initial position and a center point of the tooth in a subsequent position may be determined when calculating a change in position, and calculating the changes in position can further include calculating root movement measurements of the first tooth (e.g., canine tooth) and the second tooth (e.g., posterior tooth). For example, based on root movement measurements, an amount (e.g., an average amount) of mesial and/or distal movement of the first and second teeth in a quadrant can be calculated. This amount can be compared to one or more thresholds to determine an amount of A-P correction, as will be discussed further herein.

The changes in position of each of the first tooth and the second tooth can be projected onto a reference line (e.g., an arch line) at 206. For instance, the center point of the tooth (e.g., the first and/or second tooth) at its initial and subsequent positions can be projected onto the reference line.

For example, using the change in position (e.g., distance) between the initial and subsequent position of the tooth, as well as the reference line, a perpendicular projection can be made onto the reference line from the center of the subsequent tooth position. This will be discussed further herein with reference to FIG. 3.

At 208, an average change in position on the reference line for the first tooth and the second tooth is calculated. The average change in position can include adding the change in position between initial and subsequent positions of the first tooth to the change in position between initial and subsequent positions of the second tooth, and dividing the total by two. For example, if the change in position of the first tooth is 4.0 millimeters, and the change in position of the second tooth is 5.0 millimeters, the average change in position is 4.0 mm+5.0 mm/2=4.5 mm.

The dental treatment difficulty is determined at 212 based on the average changes in position on the reference line. The determined dental treatment difficulty can represent an estimation of treatment difficulty of A-P correction, and the results can be presented as a difficulty level and/or quantity.

For example, difficulty levels may be assigned colors to, for example, aid the treatment professional in discerning the level of difficulty. For instance, a difficulty level "black" can include an average change in position from a reference line of 4.0 millimeters or more.

This may be a higher level than a "blue" difficulty level that includes an average change in position of 2.0 to 4.0 millimeters. "Blue" may be a higher treatment difficulty level than "green," which may include an average change in position of 1.0 to 2.0 millimeters. In some such embodiments, an average change in position of less than one millimeter may receive no color label.

In some embodiments, determining the dental treatment difficulty may include comparing the average change in position of the first and second teeth to a threshold change in position. For example, if the threshold change in position is 4.0 millimeters, and the calculated average change in position is greater than 4.0 millimeters, then there is A-P correction movement in the quadrant containing the first and second teeth. If the calculated average change in position is less than the threshold 4.0 millimeters, there is no A-P correction movement in the quadrant containing the first and second teeth. An amount of A-P correction can be determined using this information.

A determination regarding whether to adjust a dental treatment plan can also be made based on the threshold comparison. For example, if an original treatment plan was based on an assumption of A-P correction movement in the quadrant, but it is determined that the calculated average change in position is less than a threshold, the original treatment plan may be changed. This may occur, for example, if it is determined that the treatment plan is too difficult, for instance, for a recommended treatment provider to perform.

In some embodiments, a determined dental treatment difficulty can be compared to a table of difficulty ranges to determine a level of difficulty for a quadrant of teeth, among other benefits. For example, using average mesial and/or distal movement of first and second teeth, as well as a table of treatment difficulty ranges, an estimate of the level of difficulty of treatment for a quadrant of teeth can be determined. This difficulty level and/or a calculated value of A-P correction can be presented to a treatment provider. The dental treatment difficulty level may govern the type of treatment provided to a patient and/or the treatment professional recommended to perform the treatment, as well as the length of treatment.

A determination regarding whether to adjust the dental treatment plan can be made based on a comparison of the dental treatment difficult to a treatment provider skill level. For example, a treatment provider may have certain abilities and/or a certain level of skill that allows for him or her to provide a particular level of treatment (e.g., at or below a certain treatment difficulty level). A treatment provider's skill level may be determined, for example, by a self-ranking, a test score and/or performance, and/or a rating by an appliance provider.

If the provider's skill level does not meet or exceed the determined treatment difficulty level, the provider may not be able to perform the treatment. However, the dental treatment plan may be adjusted based on the comparison, or a different treatment professional may be recommended.

For example, the patient and the provider may choose to alter the treatment in order for it to fall into the provider's skill level. For instance, dental treatment difficulty, a type of dental treatment, and/or a duration of dental treatment may be adjusted based on the adjusted dental treatment plan.

Figure 3:
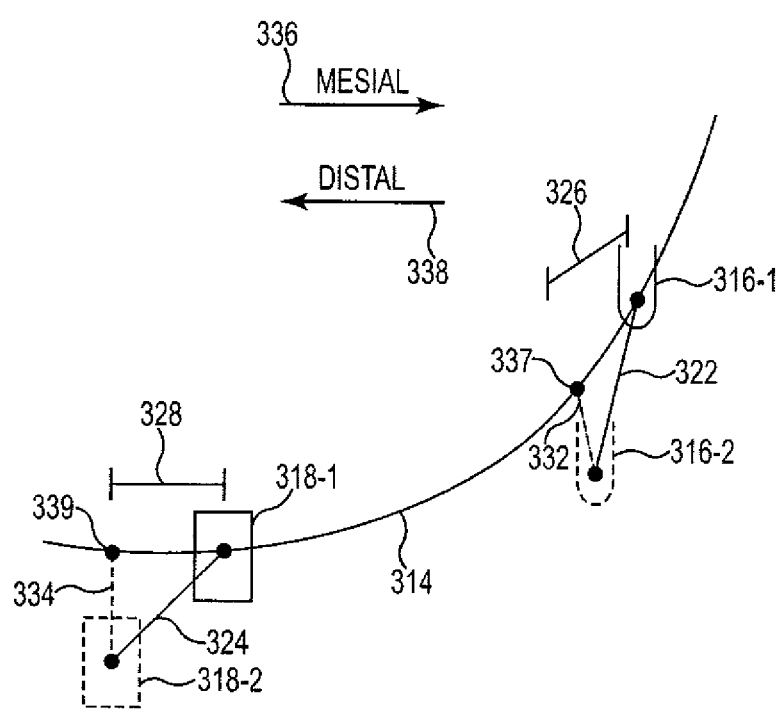
FIG. 3 illustrates an example of changes in position of teeth on a reference line according to one or more embodiments of the present disclosure.

FIG. 3 illustrates an example of changes in position of teeth on a reference line 314 according to one or more embodiments of the present disclosure. In an example, reference line 314 can be an arch line.

As indicated by arrows 336 and 338, respectively, teeth can move in mesial and distal directions. In the example illustrated in FIG. 3, a first tooth (e.g., canine tooth) has an initial mouth position at 316-1 and a subsequent position at 316-2.

The distance between the center of the tooth at its initial position 316-1 and its subsequent position 316-2 is indicated by vector 322. The center of the tooth at its initial position 316-1 is located on reference line 314, while the center of the tooth at its subsequent position 316-2 is located some distance 332 from reference line 314.

The projected change in position of the first tooth from initial position 316-1 to subsequent position 316-2 can be projected onto reference line 314 at point 337. Point 337 can be located a distance 326 along reference line 314 from the center point of the initial position 316-1.

In the example illustrated in FIG. 3, a second tooth (e.g., posterior tooth) has an initial mouth position at 318-1 and a subsequent position at 318-2. The distance between the center of the tooth at its initial position 318-1 and its subsequent position 318-2 is indicated by vector 324.

The center of the tooth at its initial position 318-1 is located on reference line 314, while the center of the tooth at its subsequent position 318-2 is located some distance 334 from reference line 314. The projected change in position of the first tooth from initial position 318-1 to subsequent position 318-2 can be projected onto reference line 314 at point 339. Point 339 can be located a distance 328 along reference line 314 from the center point of the initial position 318-1.

Figure 4:
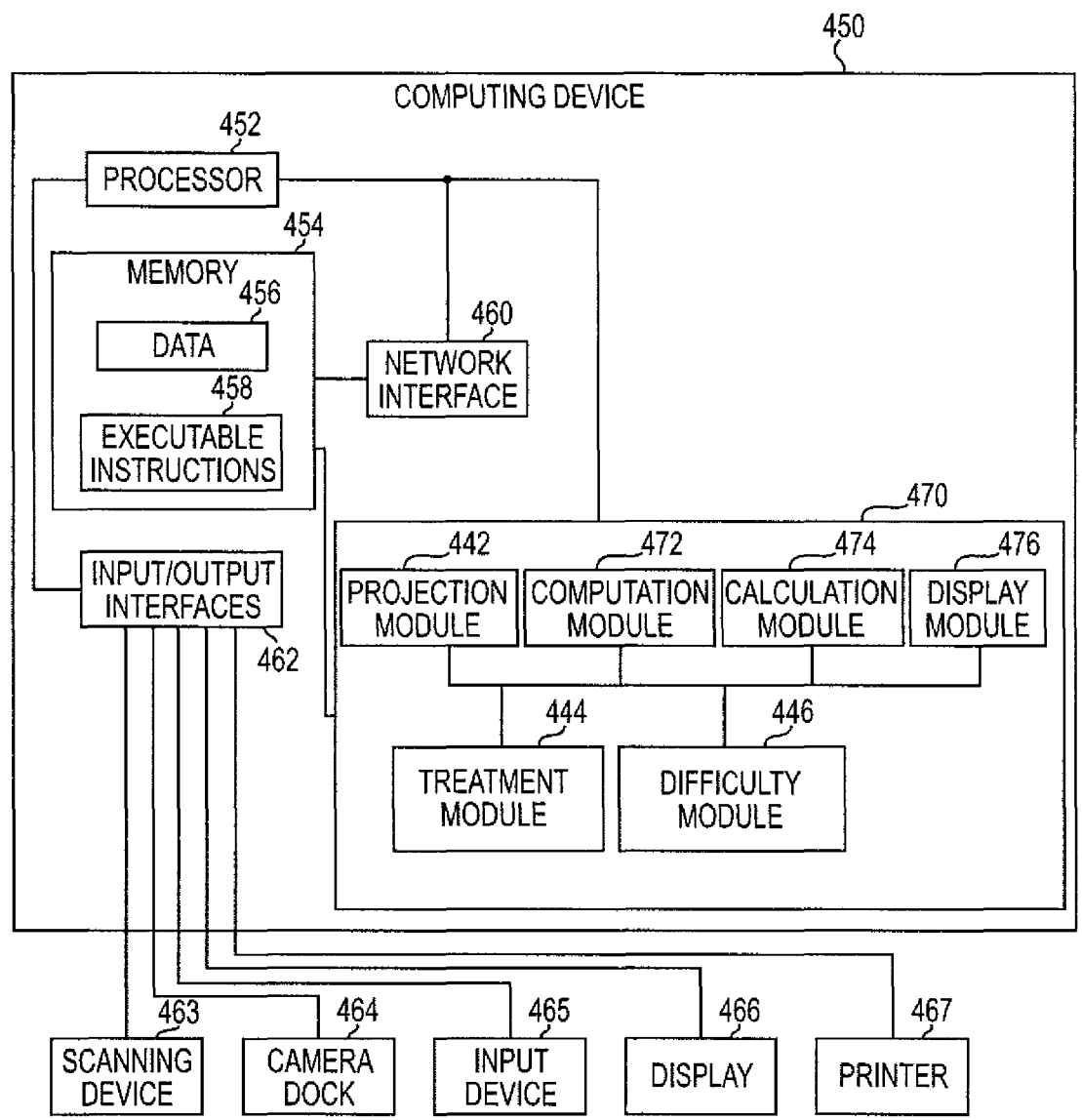
FIG. 4 illustrates an example system for determining a dental treatment difficulty according to one or more embodiments of the present disclosure.

In the example illustrated in FIG. 3, the first tooth can be a canine, and the second tooth can be a first molar. The use of the canine and the first molar as reference may be beneficial, for example, because spacing of each of one or more teeth between the canine and the first molar can be captured FIG. 4 illustrates an example system for determining a dental treatment difficulty according to one or more embodiments of the present disclosure. In the system illustrated in FIG. 4, the system includes a computing device 450 having a number of components coupled thereto. The computing device 450 includes a processor 452 and memory 454. The memory can include various types of information including data 456 and executable instructions 458, as discussed herein.

Memory and/or the processor may be located on the computing device 450 or off the device, in some embodiments. As such, as illustrated in the embodiment of FIG. 4, a system can include a network interface 460. Such an interface can allow for processing on another networked computing device, can be used to obtain information about the patient, and/or can be used to obtain data and/or executable instructions for use with various embodiments provided herein.

As illustrated in the embodiment of FIG. 4, a system can include one or more input and/or output interfaces 462. Such interfaces can be used to connect the computing device with one or more input and/or output devices.

For example, in the embodiment illustrated in FIG. 4, the system can include connectivity to a scanning device 463, a camera dock 464, an input device 465 (e.g., a keyboard, mouse, etc.), a display device 466 (e.g., a monitor), a printer 467, and/or one or more other input devices 465. The input/output interface 462 can receive executable instructions and/or data, storable in the data storage device (e.g., memory 454), representing a digital dental model of a patient's dentition and/or initial and subsequent positions of a first tooth (e.g., a canine) and second tooth (e.g., a posterior tooth).

In some embodiments, the scanning device 463 can be configured to scan one or more physical molds of a patient's dentition. In one or more embodiments, the scanning device 463 can be configured to scan the patient's dentition directly. The scanning device 463 can be configured to input data into the computing device wherein the data can be provided to the application modules 470.

In some embodiments, the camera dock 464 can receive an input from an imaging device (e.g., a two-dimensional or three-dimensional imaging device) such as a digital camera, a printed photograph scanner, or other suitable imaging device. The input from the imaging device can, for example, be stored in memory 454.

The processor 452 can execute instructions to provide a visual indication of a treatment plan and/or dental treatment difficulty on the display 466. The computing device 450 can be configured to allow a treatment professional or other user to input treatment goals. Input received can be sent to the processor 452 as data and/or can be stored in memory 454.

Such connectivity can allow for the input and/or output of data and/or instructions among other types of information. Although some embodiments may be distributed among various computing devices within one or more networks, such systems as illustrated in FIG. 4, can be beneficial in allowing for the capture, calculation, and/or analysis of information discussed herein.

The processor 452, in association with the data storage device (e.g., memory 454), can be associated with data and/or application modules 470. The processor 452, in association with the memory 454, can store and/or utilize data and/or execute instructions to provide a number of application modules for determining a dental treatment difficulty. As used herein, a module can be a stand alone program or portion of a program or can be a set of code that provides a particular functionality and may not be stand alone and may not even include instructions interspersed within a set of code.

Application modules can include a computation module 472, a calculation module 474, a projection module 442, a treatment module 444, a difficulty module 446, and/or a display module 476.

Computation module 472 can, for example, be configured to compute a change in position between an initial position and a subsequent position of each of a first (e.g., canine) and second (e.g., posterior) tooth. Projection module 442 can be configured to project the changes in position for each of the first and second tooth onto a reference line, and calculation module 474 can be configured to calculate an average change in position of the first tooth and second tooth in relation to the reference line.

Difficulty module 446 can be configured to determine the dental treatment difficulty based on the average change in position, and treatment module 444 can be configured to adjust a dental treatment plan based on a comparison of the dental treatment difficulty and a provider skill level. Difficulty module 446 can be further configured to determine the dental treatment difficulty based on a calculated A-P correction dental treatment plan. Display module 476 can be configured to display a change in position of the first tooth and a change in position of the second tooth, the projected changes, the average change in position, the dental treatment difficulty, and/or the adjusted dental treatment plan.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A computing device implemented method of determining a dental treatment difficulty, the computing device implemented method comprising: receiving a digital scan of a patient's dentition;
    gathering, from a first virtual dental model rendered from the scan, first positions of a first tooth and a second tooth, the first tooth comprising an anterior tooth in the patient's dentition and the second tooth comprising a posterior tooth of the patient's dentition;
    gathering, from a second virtual dental model, second positions of the first tooth and the second tooth in accordance with an orthodontic treatment plan;
    determining a reference line including connecting a first reference point for the first position of the first tooth and a second reference point for the first position of the second toothy wherein the second position of the first tooth and the second position of the second tooth are located a distance from the reference line;
    projecting a change in position of the first tooth from its first position to its second position;
    determining a first distance along the reference line by projecting the second position of the second tooth onto the reference line;
    projecting a change in position of the second tooth from its first position to its second position;
    determining a second distance along the reference line by projecting the second position of the second tooth onto the reference line
    and assigning to the patient's dentition one or more anterior-posterior correction treatment difficulty levels based on whether one or more of the first distance and the second distance exceed one or more orthodontic treatment thresholds.

2. The method of claim 1, wherein a type of dental treatment to be performed is determined based on the one or more anterior-posterior correction treatment difficulty levels.

3. The method of claim 1, wherein a duration of dental treatment to be performed is determined based on the one or more anterior-posterior treatment difficulty levels.

4. The method of claim 1, further comprising:
    providing instructions to display, via a display module, a virtual representation of an orthodontic treatment difficulty based on the one or more anterior-posterior correction treatment difficulty levels;
    adjusting the orthodontic treatment plan based on a comparison of the orthodontic treatment difficulty to a skill level of a treatment professional; and
    providing instructions to display, via the display module, the adjusted orthodontic treatment plan for use in treating the patient.

5. The method of claim 1, wherein the reference line has an arch shape.

6. A non-transitory computer-readable medium having executable instructions that can be executed by a processor to cause a computing device to: receive a digital scan of a patient's dentition;
    gather, from a first virtual dental model rendered from the scan, first positions of a first tooth and a second tooth, the first tooth comprising an anterior tooth in the patient's dentition and the second tooth comprising a posterior tooth of the patient's dentition;
    gather, from a second virtual dental model, second positions of the first tooth and the second tooth in accordance with an orthodontic treatment plan;
    determine a reference line including connecting a first reference point for the first position of the first tooth and a second reference point for the first position of the second toothy wherein the second position of the first tooth and the second position of the second tooth are located a distance from the reference line;
    project a change in position of the first tooth from its first position to its second position;
    determine a first distance along the reference line by projecting the second position of the first tooth onto the reference line;

project a change in position of the second tooth from its first position to its second position;

determine a second distance along the reference line by projecting a change in position of the second tooth from its first position to second position onto the reference line;

and assign to the patient's dentition one or more anterior-posterior correction treatment difficulty levels based on whether one or more of the first distance and the second distance exceed one or more orthodontic treatment thresholds.

7. The non-transitory computer-readable medium of claim 6, wherein the one or more anterior-posterior correction treatment difficulty levels is compared to a number of anterior-posterior correction treatment difficulty level ranges to determine an anterior-posterior correction treatment difficulty level for a quadrant of teeth.

8. The non-transitory computer-readable medium of claim 6, comprising instructions to calculate root movement measurements of the first tooth and the second tooth.

9. The non-transitory computer-readable medium of claim 6, comprising instructions to:
provide instructions to display, via a display module, a virtual representation of an orthodontic treatment difficulty based on the one or more anterior-posterior correction treatment difficulty levels; and
adjust the orthodontic treatment plan based on a comparison of the orthodontic treatment difficulty to a skill level of a treatment professional; and provide instructions to display, via the display module, the adjusted orthodontic treatment plan for use in treating the patient.

10. The non-transitory computer-readable medium of claim 6, wherein the reference line has an arch shape.

11. A system for determining a dental treatment difficulty, comprising:
a memory having computer-readable instructions stored thereon; and
a processor coupled to the memory to execute the computer-readable instructions to:
receive a digital scan of a patient's dentition;
gather, from a first virtual dental model rendered from the scan, first positions of a first tooth and a second tooth, the first tooth comprising an anterior tooth in the patient's dentition and the second tooth comprising a posterior tooth of the patient's dentition;
gather, from a second virtual dental model, second positions of the first tooth and the second tooth in accordance with an orthodontic treatment plan;
determine a reference line connecting a first reference point for the first position of the first tooth and a second reference point for the first position of the second tooth wherein the second position of the first tooth and the second position of the second tooth are located a distance from the reference line;
determine a first distance along the reference line by projecting a change in position of the first tooth from its first position to its second position onto the reference line, and a second distance along the reference line by projecting a change in position of the second tooth from its first position to its second position onto the reference line; and
assign to the patient's dentition one or more anterior-posterior correction treatment difficulty levels based on whether one or more of the first distance and the second distance exceed one or more orthodontic treatment thresholds.

12. The system of claim 11, wherein the computer-readable instructions further comprise instructions to:
provide instructions to display, via a display module, a virtual representation of an orthodontic treatment difficulty based on the one or more anterior-posterior correction treatment difficulty levels;
adjust the orthodontic treatment plan based on a comparison of the orthodontic treatment difficulty to a skill level of a treatment professional; and
provide instructions to display, via the display module, the adjusted orthodontic treatment plan to treat the patient.

13. The system of claim 11, wherein the reference line has an arch shape.

14. A computing device implemented method comprising:
gathering a first dental model representing a dentition of a patient at a first stage of an orthodontic treatment plan, the first dental model including a first representation of an anterior tooth in an anterior portion of the dentition and a first representation of a posterior tooth in a posterior portion of the dentition, wherein the first dental model includes a first initial reference point for an initial position of the anterior tooth and a second initial reference point for an initial position of the posterior tooth;
gathering a second dental model representing the dentition of the patient at a second stage of the orthodontic treatment plan, the second dental model including a second representation of the anterior tooth and a second representation of the posterior tooth, wherein the second dental model includes a first subsequent reference point for a subsequent position of the anterior tooth and a second subsequent reference point for a subsequent position of the posterior tooth;
determining a reference line a connecting the first initial reference point and the second initial reference point, wherein the first and second subsequent reference points are located a distance from the reference line;
projecting a change in position of the anterior tooth from its first position to its second position;
determining a first distance along the reference line by projecting the subsequent position of the anterior tooth onto the reference line,
projecting a change in position of the posterior tooth from its first position to its second position;
determining a second distance along the reference line by projecting the subsequent position of the posterior tooth onto the reference line;
assigning an orthodontic treatment difficulty identifier to the dentition of the patient based on whether one or more of the first distance and the second distance exceed one or more treatment thresholds.

15. The computing device implemented method of claim 14, further comprising:
providing instructions to display, via a display module, a virtual representation of an orthodontic treatment difficulty based on the orthodontic treatment difficulty identifier to adjust the orthodontic treatment plan based on a comparison of the orthodontic treatment difficulty to a skill level of a treatment professional, wherein the skill level of the treatment professional is determined by an appliance provider, and wherein the orthodontic treatment difficulty is above the skill level of the treatment professional; and provide instructions to display, via the display module, the adjusted orthodontic treatment plan to treat the patient.

16. The computing device implemented method of claim 14, wherein the reference line has an arch shape.

17. The computing device implemented method of claim 14, wherein determining whether the one or more treatment thresholds are exceeded comprises calculating an average of the first distance and the second distance.

18. The computing device implemented method of claim 14, further comprising estimating a treatment difficulty of the orthodontic treatment plan based on the first distance and the second distance.

* * * * *